United States Patent [19]

Pohl

[11] Patent Number: 4,703,751
[45] Date of Patent: Nov. 3, 1987

[54] METHOD AND APPARATUS FOR RESECTING A DISTAL FEMORAL SURFACE

[76] Inventor: Kenneth P. Pohl, 5692 Far Hills Ave., Dayton, Ohio 45429

[21] Appl. No.: 844,923

[22] Filed: Mar. 27, 1986

[51] Int. Cl.$^4$ .................. A61B 17/00; A61B 17/56
[52] U.S. Cl. .................. 128/92 VW; D24/26; 128/303 R; 128/92 VY; 128/92 R
[58] Field of Search ............. 128/303 R, 92 R, 305, 128/317, 92 VY, 92 YV, 92 VW; 623/16, 18, 23; 83/767, 764; D24/26

[56] References Cited

U.S. PATENT DOCUMENTS

| | | | |
|---|---|---|---|
| 4,457,307 | 7/1984 | Stillwell | 128/305 X |
| 4,502,483 | 3/1985 | Lacey | 128/303 R |
| 4,524,766 | 6/1985 | Petersen | 128/92 |
| 4,567,885 | 2/1986 | Androphy | 128/303 R X |
| 4,646,729 | 3/1987 | Kenna et al. | 128/92 VW |

Primary Examiner—Richard J. Apley
Assistant Examiner—Howard Flaxman
Attorney, Agent, or Firm—Biebel, French & Nauman

[57] ABSTRACT

A method and apparatus for resecting a distal femoral surface in which an intramedullary rod is inserted through the distal surface of the femur and along the femoral shaft access, leaving a protruding end; a jig is attached to the protruding end, the jig having a shaft for receiving the rod end and a support plate attached to an end of the shaft and extending parallel to the rod; attaching a reference bar to the shaft, the bar having a pair of opposing flanges and a central opening which receives the shaft therethrough, and adjusting the bar on the shaft such that the flanges contact condylar apices of the femur; fixing the jig relative to the femur; attaching a cutting plate to the jig, the cutting plate having blade guides thereon, pivoting the cutting plate relative to the jig such that the blade guides make a predetermined angle with the rod, and securing the cutting plate to the jig; and inserting a saw blade through the blade guides to make a resection of the distal femoral surface. In the preferred embodiment, the shaft includes a plurality of bores along its length, each sized to receive the rod therethrough so that the distance between the rod and the support plate may be adjusted to accept different sized anterior femur portions. Also in the preferred embodiment, the apparatus includes a plurality of guide bars, each sized to space the blade guides a predetermined distance from the condylar apices.

11 Claims, 8 Drawing Figures

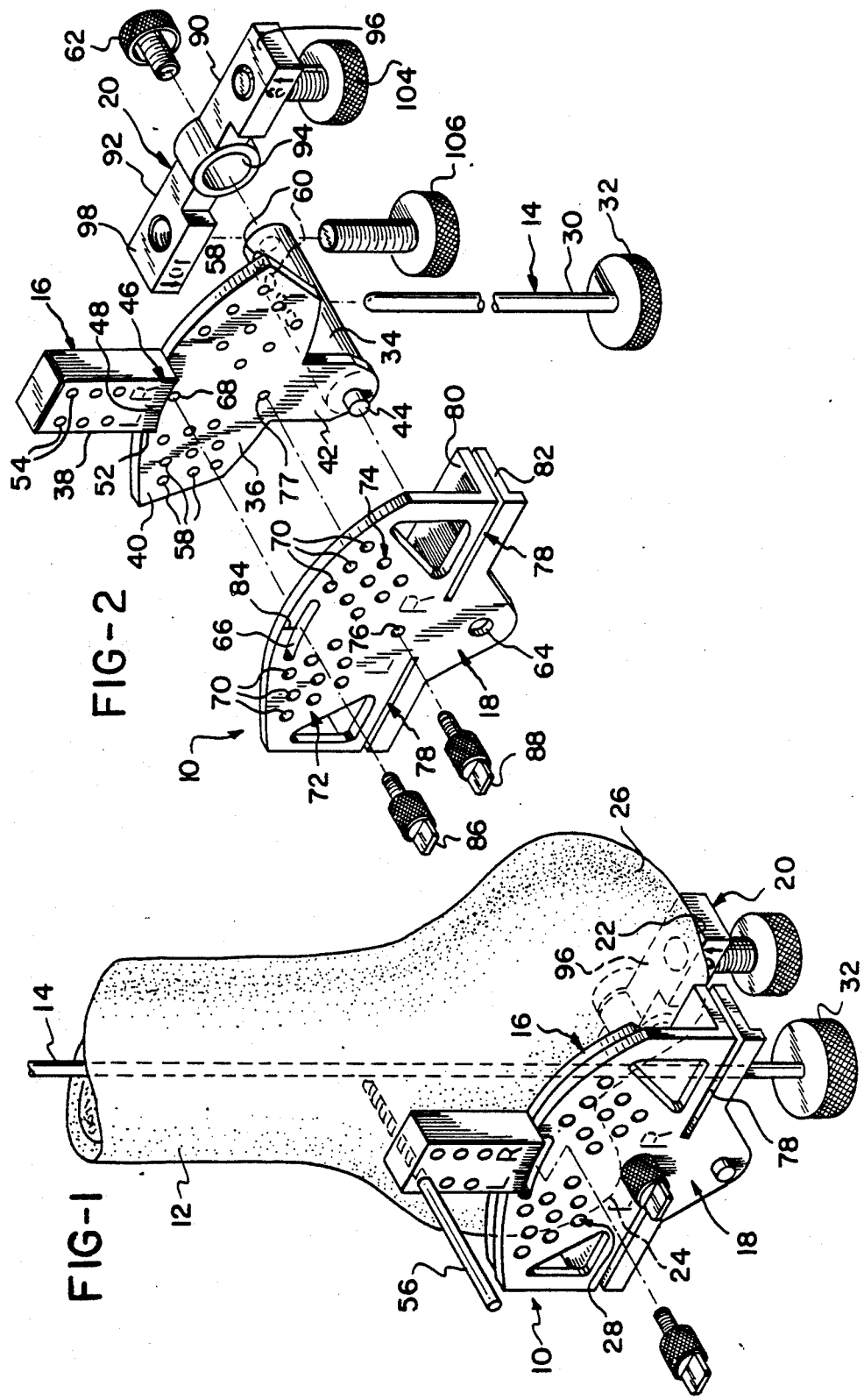

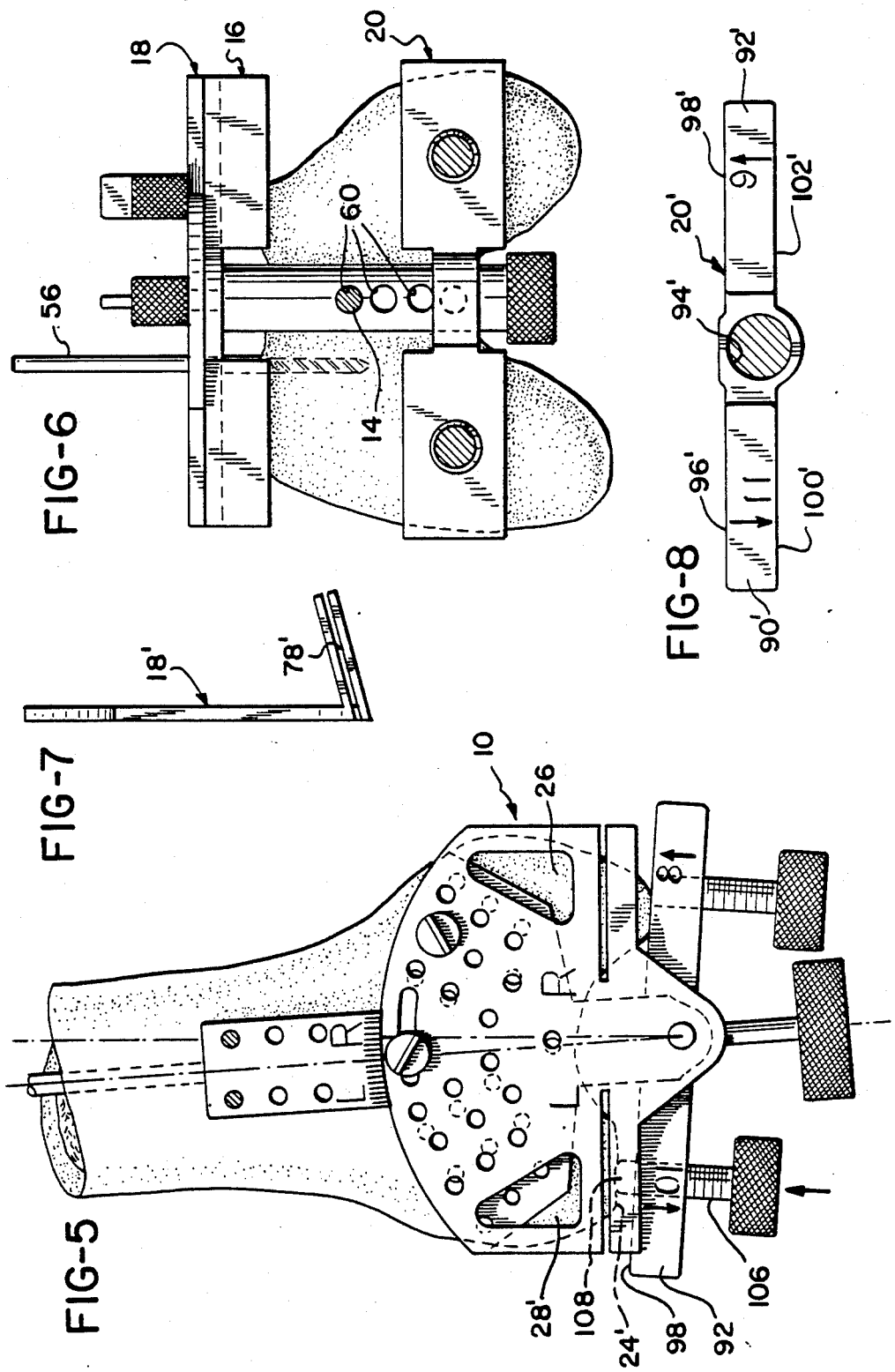

METHOD AND APPARATUS FOR RESECTING A DISTAL FEMORAL SURFACE

BACKGROUND OF THE INVENTION

The present invention relates to a method and apparatus for resecting the distal surface of a human femur to prepare that surface to accept a distal femoral prosthesis and, more particularly, to a method and apparatus for making the initial resection along the transverse axis of the knee joint which is perpendicular to the mechanical axis of the leg.

There are many types of distal femoral knee prostheses currently in use, and in many instances, a specific femoral knee prosthesis utilizes a specially designed jig which enables a surgeon to make the necessary resections to prepare the distal femoral surface to accept the prosthesis. The ultimate goal with any knee prosthesis is to approximate the natural, healthy condyles which the prosthesis is replacing. Should the prosthesis not be properly attached to the femur, the resulting misalignment could result in subsequent discomfort to the patient, walking problems, or degradation of the prosthesis.

In attaching a knee prosthesis, it is desirable to orient the prosthesis such that the transverse axis—the pivot axis of the knee joint—lies within a transverse plane which is perpendicular to the mechanical axis of the femur. The mechanical axis lies along a line which intersects the femoral head and the center of the ankle. The mechanical axis can be determined from an inspection of a radiograph of the femur to be resected. During the actual resection operation, the mechanical axis is determined by computing its angle—the valgus angle—from the femoral shaft axis. Accordingly, it is necessary to align any cutting jig or fixture properly with respect to the femoral shaft axis.

There are many jigs designed to be attached to the femur which include structure for accurately aligning the jig with the femoral shaft axis. Characteristic of such a device is the Laskin Precision Total Knee Instrumentation Assembly, manufactured by Richards Medical Company, and disclosed in the catalog entitled *Total Knee Replacement with the Tricon-M System*, published by Richards Medical Company, 1984.

The jig disclosed in that publication includes a femoral intramedullary stem which is inserted through the intercondylar notch and upwardly through the femur along the femoral shaft axis. The stem includes a bracket which supports a distal femur cutting guide. The bracket includes a first pin which extends through the cutting guide and acts as a pivot axis. A second pin is attached to the bracket and extends through an arcuate slot in the cutting guide and receives a wing nut. A boss is also attached to the bracket and extends through a second arcuate slot in the cutting guide. The second slot includes markings indicating the angle the cutting guide is pivoted from alignment with the femoral shaft axis.

The cutting guide includes pairs of opposing slots formed along its sides which are oriented to be perpendicular to a central axis of symmetry of the cutting guide. When the cutting guide is pivoted such that the central axis of symmetry lies along the mechanical axis—thereby forming the appropriate angle with the femoral shaft axis—these cutting guide slots are positioned to be perpendicular to the mechanical axis. The cutting guide is locked into the predetermined angle with the femoral shaft axis by tightening the wing nut against the upper surface of the cutting guide, which clamps it against the bracket.

The depth of the initial resection is determined by the dimensions of the particular femoral implant to be utilized. For example, a femoral implant manufactured by Richards Medical Company has a distal thickness of approximately 1.2 cm. Accordingly, the resection should usually be made a distance of 1.2 cm from the distal condylar apices. In order to position the cutting guide an appropriate distance from the distal portion of the femur, the aforementioned jig includes a resection guide, which is a flat plate that attaches to the rear or distal portion of the cutting guide.

To attach the Laskin Assembly to a femur, first the intramedullary stem is displaced into the femur until the resection guide contacts one or both the condylar apices. The jig is then secured in position during the cut by bone spikes which are inserted through openings in the cutting guide and into the femur. The flat surface resulting from such a cut, which lies along the transverse axis, serves as a reference surface from which other resections, such as the anterior and posterior resections, are made. Accordingly, it is necessary for this initial resection to be made with a high degree of precision.

A disadvantage with the aforementioned jig is that the cutting guide is held in its position along the mechanical axis by the clamping engagement of the wing nut, so that the cutting guide may move slightly from its desired position as a result of vibrations received from the moving blade of the resecting instrument, typically an electric saw.

Other types of resecting guides utilize a more positive mechanism for positioning the saw guides. For example, Lacey U.S. Pat. No. 4,502,483 discloses an apparatus for resecting a distal femoral surface which includes a main body having a first plurality of holes and a guide holder which is pivotally attached to the main body and includes a second plurality of holes. The pluralities of holes are arranged such that pairs of holes from each of the pluralities of holes come into registry with each other at predetermined degrees of inclination of the holder relative to the main body. A screw is inserted into the pair of holes in registry to lock the holder relative to the main body. The main body is attached to the femur by a clamp.

A disadvantage with both of the aforementioned types of devices is that they are not designed to compensate for severe femoral condyle deficiency, wherein one condyle is reduced in size relative to the other. With those devices, there would be a tendency to remove an insufficient amount of bone from the deficient condyle. Although the Laskin device contains multiple blade slots for varying the depth of cut, the depth of cut can be varied only on a large scale and only in predetermined increments. The Lacey device lacks altogether a mechanism for varying the depth of cut.

Another disadvantage of the aforementioned devices is that they are specifically adapted to the shapes of a particular joint prosthesis, so that they may not be used to perform resections to prepare the femur for different types of prostheses.

Accordingly, there is a need for a method and apparatus for resecting a distal femoral surface which is sufficiently flexible to perform a resection in cases involving a severe femoral condylar deficiency. Furthermore, there is a need for a method and apparatus for resecting a distal femoral surface to accommodate different types of femoral prostheses.

SUMMARY OF THE INVENTION

The present invention is a method and apparatus for resecting a distal femoral surface which, unlike prior art methods and apparatus, is sufficiently adjustable to accommodate a distal femoral surface having a severe condylar deficiency. Furthermore, in a preferred embodiment of the invention, the apparatus is adjustable to vary the depth of cut to accommodate different types of femoral prostheses.

The apparatus includes an intramedullary rod adapted to be inserted through the distal femoral surface and extend along the femoral axis, a jig for attachment to the rod, a cutting plate, and a reference bar. The jig includes a support plate which attaches to and extends substantially parallel to the rod, and a shaft for receiving the rod. The cutting plate pivotally attaches to the support plate and includes pairs of slots for guiding a saw blade and a positive locking device for clamping the cutting plate to the support plate at a predetermined angle. The reference bar which attaches to the support plate includes a pair of opposing flanges that contact the apices of the lateral and medial condyles and thereby space the blade slots an appropriate distance from the distal end of the femur. The shaft includes a plurality of bores along its length for receiving the rod. When attaching the shaft to the rod, a bore in the shaft is selected to receive the rod so that the support plate is spaced from the rod a distance which places the support and cutting plates immediately adjacent to the anterior portion of the femur. Consequently, the blade slots can be placed in close proximity to the portion of the distal surface to be resected.

The reference bar pivots relative to the shaft so that it can be positioned to contact both the lateral and medial condyles, even in cases of severe condyle deficiency. This enables the blade guides to be positioned an appropriate distance from the apices to make the proper resection of both condyles.

In a preferred embodiment of the invention, the apparatus includes a plurality of reference bars, each being sized to position the blade slots of the cutting plate an appropriate distance from the condylar apices to make a resection for a particular type of femoral prosthesis. Also in the preferred embodiment, the locking mechanism comprises first and second pluralities of holes formed in the jig and cutting plate, respectively, and positioned so that one pair of holes comes into registry as the cutting plate is pivoted from a position of alignment with the rod and femoral shaft axis, and the apparatus includes a screw shaped to thread into the pair of holes in registry to lock the cutting plate at the selected angle. Accordingly, the blade guides can be positioned perpendicularly to the mechanical axis and the cutting plate can be locked into position relative to the jig to prevent movement during the resection process.

In the method of the invention, the initial step is to insert the rod into the femur along the femoral shaft axis. The jig is then mounted on the rod by inserting the rod through a selected bore in the shaft such that the support plate is spaced adjacent to the anterior surface of the femur. Next, the reference bar is attached to the shaft and positioned such that it contacts the lateral and medial condylar apices; it may also be necessary at this time to pivot the jig about the rod so that the bar contacts both condylar apices.

The jig is then fixed relative to the femur by inserting a drill bit through a hole in the support plate and into the femur. The cutting plate may now be attached to the jig and pivoted to an angle relative to the rod corresponding to the tibial femoral angle, which has been determined by inspection of a radiograph of the femur. The blade guides of the cutting plate are now coplanar with the transverse axis and are perpendicular to the mechanical axis of the femur. The final step in the method is to perform the initial resection by inserting a saw blade through the blade guides and making the resection.

Accordingly, it is an object of the present invention to provide a method and apparatus for performing the initial resection along the transverse axis to prepare the distal femoral surface to receive a femoral prosthesis; to provide a method and apparatus which are sufficiently flexible to compensate for severe femoral condyle deficiencies; an apparatus which is sufficiently adjustable to perform a resection for a variety of types of femoral prostheses; and an apparatus which is of relatively simple construction and can be adjusted to guide a saw blade with a high degree of precision.

Other objects and advantages will be apparent from the following description, the accompanying drawings and the appended claims.

BRIEF DESCRIPTION OF THE DRAWINGS

FIG. 1 is a perspective view of the apparatus of the claimed invention, mounted on the distal portion of the right femur;

FIG. 2 is an exploded view, in perspective, of the apparatus of FIG. 1;

FIG. 5 is a top plan view of the apparatus of FIG. 1, shown mounted on the distal end of a femur having severe femoral condyle deficiency;

FIG. 6 is a distal elevation of the apparatus of FIG. 1;

FIG. 7 is a side elevation of the cutting plate of a second embodiment of the invention; and FIG. 8 is a detail of a reference bar of a third embodiment of the invention.

DETAILED DESCRIPTION OF THE PREFERRED EMBODIMENTS

Figure 4:
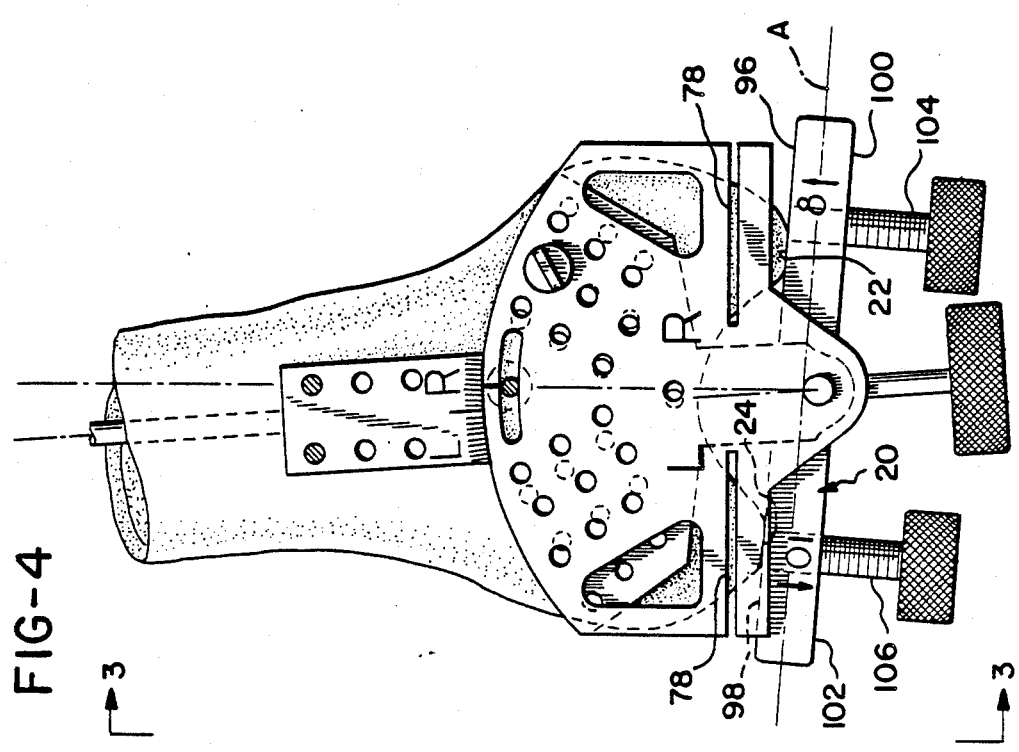
FIG. 4 is a top plan view of the apparatus of FIG. 1.

As shown in FIG. 1, the resection apparatus of the present invention, generally designated 10, is adapted to be mounted on the distal end of a femur, such as the right femur 12 shown. The apparatus 10 includes an intramedullary rod 14, a jig 16, cutting plate 18, and reference bar 20. The reference bar 20 is shown engaging the apices 22, 24 of the lateral and medial condyles 26, 28, respectively.

Figure 3:
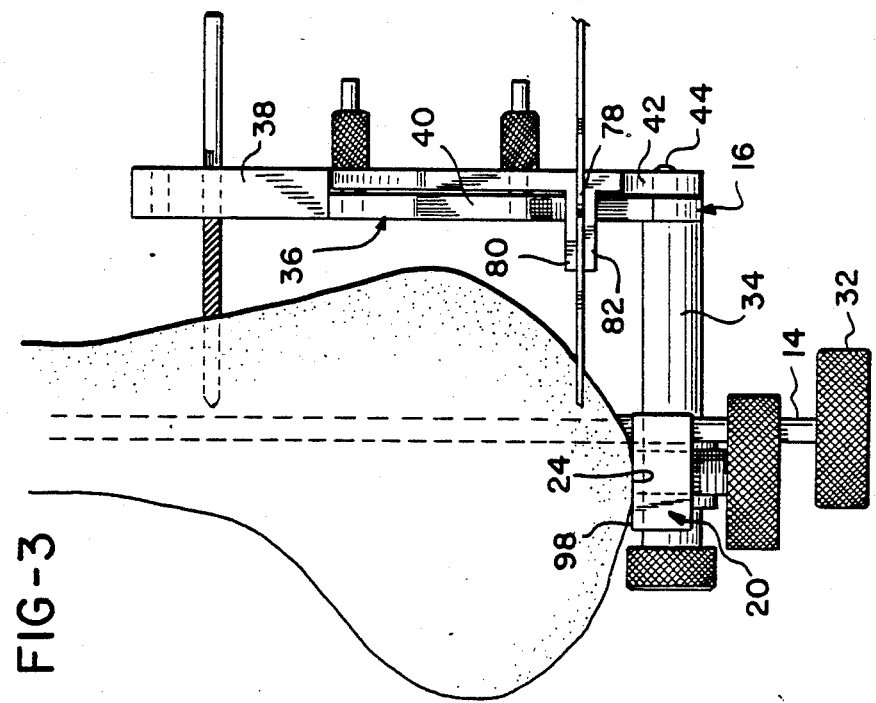
FIG. 3 is a side elevation of the apparatus of FIG. 1, shown inserted in the right femur.

As shown in FIGS. 2 and 3, the intramedullary rod 14 includes a rod portion 30 which is threaded at its distal end into a knurled knob 32. The jig 16 includes an elongate, cylindrical shaft 34 which is attached at its upper end to the distal portion of a support plate 36. The support plate 36 includes a proximal, raised portion 38 and a fan-shaped portion 40, which terminates in a tongue 42. The tongue 42 includes a raised boss 44, which is coaxial with the shaft 34.

The raised portion 38 includes indicia 46 which include a center mark 48 and marks 50 to the right and 52 to the left, indicating degrees of angular deviation from the center mark. The raised portion 38 also includes a plurality of holes 54 which, as shown in FIG. 1, are sized to receive a drill bit 56 to anchor the jig 16 in position on the femur 12. The fan-shaped portion 40 includes a plurality of holes 58 positioned in a predetermined pattern, the significance of which will be explained with respect to the cutting plate 18.

The shaft 34 includes a plurality of bores 60 which are sized to receive the intramedullary rod 14 therethrough. The bores 60 are positioned such that the intramedullary rod 14 is oriented substantially parallel to the support plate 36 and to the center mark 48 of the raised portion 38. Thus, when the rod 14 is properly inserted along the femoral shaft axis, the degree marks 50, 52 indicate the valgus angle for that particular femur. A bolt 62 having a knurled knob is threaded into the lower end of the shaft 34 to retain the guide bar 20.

The cutting plate 18 includes a hole 64 which receives the boss 44, so that the boss serves as a pivot axis of the cutting plate. The cutting plate 18 is superposed to the support plate 36 and includes an arcuate slot 66 which is in registry with a locking hole 68 on the fan-shaped portion 40.

The cutting plate 18 also includes a plurality of holes 70 which are positioned with respect to the holes 58 in the fan-shaped portion 40 such that a single pair of holes of the cutting plate and jig 16 come into registry for each degree of valgus angle. The plurality of holes 70 is divided into left 72 and right 74 groupings, so that the apparatus 10 may be utilized with either the right or left femur. There is also a zeroing hole 76 which is in registry with a corresponding hole 77 in the support plate 36 when the cutting plate 18 is aligned with the rod 14.

The distal portion of the cutting plate 18 includes a pair of rectilinear blade slots 78 which are formed by pairs of front and rear panels 80, 82, respectively. The blade slots 78 are oriented to be perpendicular to the central axis of the cutting plate 18, denoted by alignment mark 84 adjacent to the arcuate slot 66.

The plurality of holes 58 in the fan-shaped portion 40 are threaded and receive screws 86, 88. Typically, screw 86 is threaded into the locking hole 68 through the arcuate slot 66, and screw 88 is inserted through a selected one of the plurality of holes 70 and threaded into its corresponding one of the holes 54 in the fan-shaped portion. This two-point locking mechanism rigidly secures the cutting plate 18 against the support plate 36, thereby locking the position of the blade slot 78 relative to the jig 16 and rod 10.

The reference bar 20 includes a pair of opposing flanges 90, 92 and a central opening 94 sized to receive the shaft 34 therethrough so that the reference bar may be slidably and pivotally positioned on the shaft 34. The central opening is offset from the central plane of symmetry of the reference bar 20, denoted by line A (see FIG. 4), so that the reference bar may be pivoted about the shaft to place faces 96, 98 in position to contact the condyles 26, 28, or pivoted to position faces 100, 102 to contact the condyles and thereby vary the distance between the portion of the reference bar contacting the condyles and the blade slots 78.

As shown in FIGS. 1, 3 and 4, this opening is positioned such that faces 96, 98 of the reference bar 20 space the blade slots 78 a distance of 8 mm from the condylar apices 22, 24. Similarly, the reference bar 20 may be pivoted 180° about shaft 34 to place faces 100, 102 in contact with the apices 22, 24, in which case the blade slots 78 are spaced 10 mm from the condylar apices.

As shown in FIG. 8, an alternate reference bar 20' may be used. Bar 20' is shaped such that its central opening 94' is offset to make the faces 96', 98', and opposing faces 100', 102' of flanges 90', 92'; distances of 9 mm and 11 mm, respectively. In the preferred embodiment, the apparatus 10 would include a plurality of such reference bars 20, each poviding two different spacings of the blade slots 78 from the condylar apices 22, 24.

As shown in FIGS. 2 and 4, the reference bar 20 also includes bolts 104, 106 which are threaded through the flanges 90, 92, respectively. The bolts 104, 106 provide a measure of fine adjustment of the distance of the blade slots 78 from the condylar apices 22, 24. Furthermore, as shown in FIG. 5, the bolts allow the apparatus 10 to compensate for instances of severe condylar deficiency. In such an instance, the face 98, adjacent to the deficient condyle 28' is "backed away" from that condyle by displacing the bolt 106 through the flange 92 until the end 108 of the bolt contacts the condylar apex 24'. This action draws the blade slots 78 slightly closer to the distal femoral surfaces so the resulting cut is not quite as deep. This is advantageous since it is undesirable to remove an excessive amount of healthy material from the larger condyle 26.

Since the opening 94 is positioned at the center of the reference bar 20 (see FIG. 2), the resultant displacement of the slots 78 toward the distal surface by the displacement of the bolt 106 will be less than the total displacement of the bolt, since the reference bar, in effect, is being made to pivot about its contact with the larger condyle 22.

The method of the invention is as follows. It should be understood that, prior to performing this method, a radiograph of the femur to be resected should be taken to determine the precise location of the femoral shaft axis, the mechanical axis, and the resultant tibial femoral (valgus) angle. The initial resection to be performed by the method of the invention will lie along a transverse plane which is perpendicular to the mechanical axis at the point it intersects the femoral shaft axis. Also prior to performing the method of the invention, the leg is prepared in a conventional manner to expose the distal femoral surface.

In the initial step of the method of the present invention, the intramedullary rod 14 is inserted through the intercondylar canal and along the femoral shaft axis, leaving the end protruding from the distal femoral surface, as shown in FIG. 1. The jig 16 is mounted on the rod 14 by inserting the end of the rod through a selected one of the bores 60 in the shaft 34. As shown in FIGS. 3 and 6, a bore is selected such that the underside of the support plate 36 is immediately adjacent to the anterior femoral surface. By inserting the rod 14 through the selected bore 60, the jig is positioned parallel to the rod 14. At this time, the knurled knob 32 can be threaded onto the rod end.

The reference bar 20 is now attached to the shaft 34 of the jig 16 by inserting the shaft through the central opening 94. The reference bar 20 is displaced along the shaft 34 until the selected faces (faces 96, 98 shown in this instance in FIG. 4) are in registry with the condylar apices 22, 24. This may also require that the jig be pivoted slightly about the rod 14. At this time, the bolts 104, 106 may be adjusted, if necessary. The jig 14 and reference bar 20 are now in position, and the jig 16 is fixed in position by inserting drill bit 56 through a selected one of the holes 54 and drilling it into the femur.

During this procedure, it may be necessary to hold the reference bar 20 in position as well as the jig 16.

The cutting plate 18 is now attached by placing it over the fan-shaped portion 40 of the jig 16 so that the boss 44 extends through the hole 64. Since a right femur is being resected in the drawing figures, the cutting plate 18 is pivoted to the right to the appropriate valgus angle calculated from the radiograph. At this position, the appropriate ones of the holes 58 and 70 will come into registry and receive the screw 88 to lock the cutting plate 18 into position. At this time, the screw 86 is inserted through the arcuate slot 66 and into the locking hole 68 to provide a second point of attachment. The apparatus 10 is now ready for the initial resection.

The final step of the method comprises inserting a flat saw blade (FIG. 3) through the slots 78 of the cutting plate 18 to make the resection. The resultant resection of the condyles 26, 28 is substantially flat, and is coplanar with the transverse axis, which is perpendicular to the mechanical axis determined in the radiograph.

The procedure for resecting the distal femoral surface for the left femur is the same, except that the cutting plate 18 is pivoted so that the left grouping 72 of holes moves into registry with the underlying holes 58 in the jig 16.

In some instances, the shape of the condylar prosthesis makes it necessary to perform a resection which forms an angle with the mechanical axis that is not perpendicular, when viewed from a side elevation, to the mechanical axis. In such instances, a cutting plate 18' as shown in FIG. 8 is utilized, in which the blade slots 78' are coplanar with one another but lie at an angle of less than 90° with the remainder of the cutting plate and underlying fan-shaped portion of the jig 16. Accordingly, in a preferred embodiment of the apparatus 10, one or more alternate cutting plates 18, 18' are included to increase the applicability of the apparatus. However, the method of operation remains the same.

While the forms of apparatus herein described constitute preferred embodiments of this invention, it is to be understood that the invention is not limited to these precise forms of apparatus, and that changes may be made therein without departing from the scope of the invention.

What is claimed is:

1. An apparatus for resecting a distal femoral surface, comprising:
    rod means adapted to be inserted through the distal femoral surface and extend, along the femoral axis;
    jig means attached to said rod means, said jig means including a shaft having a plurality of bores therealong shaped to receive an end of said rod means slidably and pivotally therethrough, and a support plate attached to an end of said shaft and extending substantially parallel to said rod means when said rod means is inserted in a selected one of said bores;
    cutting plate means pivotally attached to said support plate, and including slot means for guiding a saw blade to make a resection, and means for locking said plate means against said support plate such that said slot means makes a predetermined angle with said rod means; and
    a reference bar attached to said shaft, said reference bar having a central opening therethrough shaped to receive said shaft slidably and rotatably therethrough, said bar also including a pair of opposing flanges located relative to said opening such that said bar may be positioned on said shaft to contact apices of of lateral and medial condyles and thereby to space said slot means a predetermined distance from a distal end of an associated femur.

2. The apparatus of claim 1 wherein said flanges each include first and second opposing faces, said first faces being coplanar with each other and spaced from said opening a first predetermind distance, and said second faces being coplanar with each other and spaced from said opening a second predetermined distance greater than said first distance, whereby a spacing of said slot means from condylar apices of an associated femur may be varied by placing said first or said second faces in contact therewith.

3. The apparatus of claim 1 wherein said jig means includes an extension having a plurality of holes therethrough, and means received in said holes for fixing said jig means in position relative to an associated femur.

4. The apparatus of claim 3 wherein said extension extends outwardly from said jig means and is oriented parallel to said rod means when said rod means is inserted in a selected one of said bores.

5. The apparatus of claim 1 wherein said jig means includes a pivot pin positioned to be coaxial with said shaft and extend outwardly from an end thereof; and said cutting plate is journaled on said pin.

6. The apparatus of claim 1 wherein each of said flanges includes bolt means threaded therethrough, such that displacement of said bolt means effects relatively fine adjustments in said spacing of said slot means.

7. The apparatus of claim 1 including said jig means having a first plurality of holes, each corresponding to a degree of inclination of said slot means from a position of perpendicularity to said rod means; said cutting plate means includes a second plurality of holes, each corresponding to a degree of inclination of said slot means from a position of perpendicularity to said rod means, said cutting plate means being superposed to said jig means such that pivotal movement of said cutting plate means relative to said jig means causes predetermined ones of said first and second pluralities of holes to come into registry with each other at predetermined degrees of inclination of said slot means from a position of perpendicularity to said rod means; and set screw means for engaging said holes in registry and locking said cutting plate means against said jig means.

8. A method of resecting a distal femoral surface, comprising the steps of:
    (a) inserting an intramedullary rod through the distal surface of the femur and along the femoral shaft axis, leaving a protuding end;
    (b) attaching jig means to said protruding end, said jig means including a shaft for receiving said rod end, and a support plate attached to an end of said shaft and extending substantially parallel to said rod means;
    (c) attaching a reference bar to said shaft, said bar having a central opening receiving said shaft and a pair of opposing flanges, and adjusting said bar on said shaft such that said flanges contact condylar apices of said femur;
    (d) fixing said jig.means relative to said femur;
    (e) attaching cutting plate means to said jig means, said cutting plate means having blade guides thereon, pivoting said cutting plate means relative to said jig means such that said blade guides make a predetermined angle with said rod, and said cutting plate means to said jig means; and (f) inserting a saw blade through said blade guides to make a resection of the distal femoral surface.

9. The method of claim 8 wherein said shaft includes a plurality of bores therealong, each sized to receive said rod therethrough, and said jig attaching step (b) includes selecting one of said bores to receive said rod therethrough such that said support plate is adjustably positionable from said rod a distance sufficient to receive an anterior portion of a femur therebetween.

10. The method of claim 8 wherein said fixing step (d) includes the step of pivoting said jig means about said rod such that each of said flanges of said reference bar contacts a condylar apex.

11. The method of claim 8 wherein said flanges each include bolt means threaded therethrough, and said reference bar attaching step (c) includes the step of displacing said bolt means toward said condylar apices to decrease a depth of cut of said saw blade into said condyles.

* * * * *